US009481630B2

(12) United States Patent
Oh et al.

(10) Patent No.: US 9,481,630 B2
(45) Date of Patent: Nov. 1, 2016

(54) INGENANE-TYPE DITERPENE COMPOUND, AND PHARMACEUTICAL COMPOSITION FOR TREATING OR PREVENTING VIRAL INFECTIOUS DISEASES CONTAINING SAME

(71) Applicant: KOREA RESEARCH INSTITUTE OF BIOSCIENCE AND BIOTECHNOLOGY, Daejeon (KR)

(72) Inventors: Sei Ryang Oh, Daejeon (KR); Jae Wha Kim, Daejeon (KR); Hyeong Kyu Lee, Daejeon (KR); Piseth Khiev, Daejeon (KR); Doo Young Kim, Daejeon (KR); Jung Hee Kim, Daejeong (KR); Jae Sung Song, Daejeon (KR); Kyung Seop Ahn, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 101 days.

(21) Appl. No.: 14/352,978

(22) PCT Filed: Sep. 28, 2012

(86) PCT No.: PCT/KR2012/007897
§ 371 (c)(1),
(2) Date: Jul. 28, 2014

(87) PCT Pub. No.: WO2013/058484
PCT Pub. Date: Apr. 25, 2013

(65) Prior Publication Data
US 2014/0371311 A1 Dec. 18, 2014

(30) Foreign Application Priority Data
Oct. 19, 2011 (KR) .................. 10-2011-0107175

(51) Int. Cl.
*A61K 31/22* (2006.01)
*A61K 31/23* (2006.01)
*C07C 69/33* (2006.01)
*A23L 1/30* (2006.01)
*A61K 36/47* (2006.01)

(52) U.S. Cl.
CPC .................. *C07C 69/33* (2013.01); *A23L 1/30* (2013.01); *A23L 1/3008* (2013.01); *A61K 31/22* (2013.01); *A61K 31/23* (2013.01); *A61K 36/47* (2013.01); *C07C 2103/30* (2013.01)

(58) Field of Classification Search
CPC .............................. A61K 31/22; A61K 31/23
See application file for complete search history.

(56) References Cited

U.S. PATENT DOCUMENTS 7,449,492 B2    11/2008  Aylward et al.

FOREIGN PATENT DOCUMENTS

| JP | 06-340586 A | 12/1994 |
|---|---|---|
| JP | H07-165600 A | 6/1995 |
| JP | H08-185637 A | 7/1996 |
| JP | 2005-041799 A | 2/2005 |
| KR | 10-2009-0036210 A | 4/2009 |
| KR | 10-2009-0109769 A | 10/2009 |
| WO | 2006/116897 A1 | 11/2006 |
| WO | 2008/131491 A1 | 11/2008 |
| WO | WO 2011/071849 | * 7/2011 |

OTHER PUBLICATIONS

Fujiwara et al. Arch. Virol., 1998, vol. 143, pp. 2003-2010.*
Zheng. Zhongcaoyao, 2004, vol. 35, No. 1, pp. 65-68 (English Abstract attached).*
Wu et al. Journal of Natural Products, 1991, vol. 54, No. 3, pp. 823-829.*
Fujiwara et al. Antiviral Chemistry & Chemotherapy, 1996, vol. 7, No. 5, pp. 230-236.*
Zheng Wei-Fa et al., "Cytotoxicity and antiviral activity of the compounds from Euphorbia kansui", Planta Media, Thieme Verlag, DE, vol. 64, No. 8, pp. 754-756, Dec. 1, 1988.
Zheng Wei-Fa, "Study on in vivo antiviral activity of four diterpenoids from ethanol extracts of_Euphorbia kansui", Chinese Traditional and Herbal Drugs, vol. 35, No. 1, 2004, pp. 65-68.
Wang Yu-Bo et al., "Chemical constituents from the roots of Euphorbia kansui", Zhongguo Tianran Yaowu—Chinese Journal of Natural Medicines, Zhongguo Tianran Yaowu, Nanjing, CN, vol. 5, No. 3, pp. 182-185,Jan. 1, 2007.
Piseth Khiev et al., "Ingenane-type Diterpenes with a Modulatory Effect on IFN-γ Production from the Roots of Euphorbia kansui", Archives of Pharmacal Research, vol. 35, No. 9, pp. 1553-1558, 2012.
Gao Li et al., "Anticomplement Activity of Compounds Isolated from the Roots of Euphorbia kansui", J. Korean Soc. Appl. Biol. Chem. vol. 54(2), p. 159-162, Republic of Korea, 2011.

(Continued)

*Primary Examiner* — James D Anderson
(74) *Attorney, Agent, or Firm* — Masuvalley & Partners (57) ABSTRACT

The present invention relates to an injenane-type diterpene compound derived from *Euphorbia kansui* Liou, and a pharmaceutical composition for treating or preventing viral infectious diseases, a health functional food for preventing or ameliorating viral infectious diseases and a composition for enhancing the production of interferon-gamma, which comprise the injenane-type diterpene compound. Furthermore, the present invention relates to a method for preventing or treating viral infectious diseases including administering the composition to a subject having a viral infectious disease occurrence or a risk thereof with a therapeutically effective dose.

3 Claims, 10 Drawing Sheets

(56) References Cited

OTHER PUBLICATIONS

Satoshi Nunomura et al., "3-0-(2,3-Dimethylbutanoyl)-13-0-decanoylingenol from Euphorbia kansui Suppresses IgE-Mediated Mast Cell Activation", Pharmaceutical Society of Japan, Biol. Pharm. Bull. vol. 29(2), p. 286-290, Japan, Nov. 11, 2005.
Christine A. Biron et al., "Natural Killer Cells in Antiviral Defense: Function and Regulation by Innate Cytokines", Annu. Rev. Immunol. 1999, 17:189-220.

Jamie R. Schoenborn et al., "Regulation of Interferon-γ During Innate and Adaptive Immune Response", Advances in Immunology, vol. 96, Chapter 2, p. 41-101, Elsevier Inc., 2007.
Sandra Gessani et al., "IFN-γ Expression in Macrophages and Its Possible Biological Significances", Cytokine & Growth Factor Reviews vol. 9, No. 2, p. 117-123, Great Britain, Elsevier Science Ltd, 1998.
S. Goodborn et al., "Interferons: cell signalling, immune modulation, antiviral responses and virus countermeasures", Journal of General Virology(2000), 81, p. 2341-2364, Great Britain.

* cited by examiner

INGENANE-TYPE DITERPENE COMPOUND, AND PHARMACEUTICAL COMPOSITION FOR TREATING OR PREVENTING VIRAL INFECTIOUS DISEASES CONTAINING SAME

This application is a national phase application under 35 U.S.C. §371 of International Application Serial No. PCT/KR2012/007897 filed on Sep. 28, 2012, and claims the priority under 35 U.S.C. §119 to Korean Patent Application No. 10-2011-0107175, filed on Oct. 19, 2011, which are hereby expressly incorporated by reference in their entirety for all purposes.

TECHNICAL FIELD

The present invention relates to an ingenane-type diterpene compound derived from *Euphorbia kansui* Liou, and a pharmaceutical composition for treating or preventing viral infectious diseases, a health functional food for preventing or ameliorating viral infectious diseases and a composition for enhancing the production of interferon-gamma, which comprise the ingenane-type diterpene compound. Furthermore, the present invention relates to a method for preventing or treating viral infectious diseases including administering the composition to a subject having a viral infectious disease occurrence or a risk thereof with a therapeutically effective dose.

BACKGROUND ART

The production of interferon-γ (IFN-γ) in immunocytes is an important step in early-stage self-defense and tumor control against virus and bacterial infection (Biron, C. A. et al., *Annu. Rev. Immunol.* 1999, 17, 189-220). IFN-γ is produced in natural killer (NK) and natural killer T (NKT) cells that are generally used as effector cells in regulating immune reactions (Schoenborn, J. R. et al., *Adv. Immunol.* 2007, 96, 41-101). IFN-γ expression is particularly related to a pro-inflammatory state. The biological role of cytokain IFN-γ in a defense system is well known, and the role is related to both virus replication and direct suppression of immunostimulation (Gessani, S. et al., Cytokine & Growth F. R. 1998, 9, 117-123; Goodbourn, S. et al., *J. Gen. Virol.* 2000, 81, 2341-2364).

Pharmaceutical markets have grown globally due to an increase in income, aging population, increased demand for chronic disease-related medicines, life expectancy increase and the like, and as a result, research and development on biopharmaceuticals have increased in pharmaceutical industries at home and abroad. Among other things, there has been increased demand for antiviral therapeutic agent-related research that is the base of the development of AIDS therapeutic agents, and liver disease and influenza disease therapeutic agents, which are problems needed be solved for all mankind, for the development of therapeutic agents utilizing the results of the research, and for the development of medical technologies and technologies for improving quality of life, have been increased.

A virus is a small infectious agent (average of 0.1 μm or less) that is smaller than bacteria and thereby cannot be filtered even with a bacterial filter (0.22 μm), and is an organism that has only nucleic acid (DNA or RNA) and a small number of proteins as substances needed for survival, and thereby are dependent upon hosts. As therapeutic agents for diseases caused by viruses, drugs that weaken or kill the action of viruses infested into the body are referred to as antiviral therapeutic agents.

Immunotherapy using a vaccine is currently a mainstream viral infectious disease treatment. Specifically, examples of therapeutic agents for the infectious disease caused by chlamydia (giant virus) such as trachoma and fourth venereal disease (venereal disease) comprise tetracycline and chloramphenicol, the examples of a preventive agent for influenza A-type virus include amantadine, an idoxuridine (IDU) eye bath drop was developed as a preventive agent for herpes keratitis, and vidarabine/acyclovir have received attention as a simple herpes encephalitis (encephalitis) or an immunosuppressant. Particularly, interferon is a most promising drug for viral infectious diseases, and utility thereof is currently being examined.

Lately, the preference for natural substances in treating or preventing health issues has grown globally. This trend is affecting pharmaceutical companies, in that they are producing new antimicrobial agents extracted from plants. Accordingly, research on exploring new anti-viral materials from thousands of plant types has been constantly carried out globally, and various phytochemicals having antiviral activities, such as flavonoid, terpenoid, lignan, sulfide, polyphenols, coumarin, saponin, alkaloid, polyyne, thiophene, proteins and peptides have been identified. Several volatile essential oils of generally used edible herbs, spices and herb teas also have antiviral activities. However, with the exception of a few compound groups described above, most research on the active substances of medicinal plants having antiviral activities is in its beginning stages.

*Euphorbia kansui* Liou (Euphorbiaceae) is widely distributed throughout the China and Korea mainlands. Dried roots of *Euphorbia kansui* Liou, also known as "kansui", have been used as herbal remedies for edema and ascites (Wang, L. Y. et al., *J. Nat. Prod.* 2003, 66, 630-633), and cancer (Wang, L. Y. et al., *J. Nat. Prod.* 2002, 65, 1246-1251). Through the previous studies on *Euphorbia kansui* Liou, the presence of a great number of euphan-type triterpenes (Chang, J. S. et al., *Planta Med.* 2010, 76, 1544-1549), ingenane-type diterpenes (Pan, Q. et al., *J. Nat. Prod.* 2004, 67, 1548-1551) and jatrophane-type diterpenes (Zheng, W. F. et al., *Planta Med.* 1998, 64, 754-756) was identified in the extract of *Euphorbia kansui* Liou. In addition, the samples were verified to have an anti-cancer effect (Pan, Q. et al., *J. Nat. Prod.* 2004, 67, 1548-1551), a cytostatic effect (Chang, J. S. et al., *Planta Med.* 2010, 76, 1544-1549) and an anti-allergic effect (Ott, H. H. et al., *Experientia.* 1981, 37, 88-91).

DISCLOSURE

Technical Problem

In view of the above, the inventors of the present invention have made various efforts to identify natural product-derived materials having antiviral activities, and as a result, have isolated a ingenane-type deterpene compound from *Euphorbia kansui* Liou, then verified that the compound enhances the production of interferon gamma (IFN-γ) in NK92 cells, and completed the present invention.

Technical Solution

A first object of the present invention is to provide a compound represented by Chemical Formula 1 or a pharmaceutically acceptable salt thereof.

A second object of the present invention is to provide a pharmaceutical composition for treating or preventing viral infectious diseases, which comprises a compound represented by Chemical Formula 2 or a pharmaceutically acceptable salt thereof as an active ingredient.

A third object of the present invention is to provide a health functional food for preventing or ameliorating viral infectious diseases, which comprises a compound represented by Chemical Formula 2 or a sitologically acceptable salt thereof as an active ingredient.

A fourth object of the present invention is to provide a composition for enhancing the production of interferon-gamma, which comprises a compound represented by Chemical Formula 2 or a pharmaceutically acceptable salt thereof as an active ingredient.

A fifth object of the present invention is to provide a method for preventing or treating viral infectious diseases comprising administering the composition of any one of claims 2 to 4 to a subject having a viral infectious disease occurrence or a risk thereof with a therapeutically effective dose.

Advantageous Effects

The present invention provides an injenane-type novel diterpene compound isolated from the root area of *Euphorbia kansui* Liou, and injenane-type novel diterpene-based compounds derived from *Euphorbia kansui* Liou including the novel compound have activities of inducing the production of IFN-γ in NK cells, and thereby are effective in treating or preventing viral infectious diseases.

MODE FOR DISCLOSURE

In view of the above, the present invention provides a compound represented by the following Chemical Formula 1 or a pharmaceutically acceptable salt thereof.

[Chemical Formula 1]

In the present invention, the compound represented by Chemical Formula 1 is represented by Compound 1, and a name thereof is 5-O-(2,3-dimethylbutanoyl)-13-O-dodecanoyl-20-O-deoxyingenol.

The Compound 1 is an injenane-type diterpene compound, and is a novel material that the inventors of the present invention isolated from the root area of *Euphorbia kansui* Liou. The Compound 1 may have an activity facilitating or enhancing the interferon gamma production in cells.

In addition, the present invention provides a pharmaceutical composition for treating or preventing viral infectious diseases, which comprises a compound represented by the following Chemical Formula 2 or a pharmaceutically acceptable salt thereof as an active ingredient.

[Chemical Formula 2]

In the formula,
$R_1$ is H, $R_2$ is H, $R_3$ is OCO—$(CH_2)_{10}$—$CH_3$ and $R_4$ is CO—CH($CH_3$)—CH($CH_3$)$_2$,
$R_1$ is CO—CH($CH_3$)—CH($CH_3$)$_2$, $R_2$ is H, $R_3$ is OCO—$(CH_2)_{10}$—$CH_3$ and $R_4$ is H,
$R_1$ is H, $R_2$ is OCO—$(CH_2)_8$—$CH_3$, $R_3$ is H and $R_4$ is H,
$R_1$ is CO(CH═CH)—$(CH_2)_4$—$CH_3$, $R_2$ is OAc, $R_3$ is H and $R_4$ is H,
$R_1$ is CO—CH($CH_3$)—CH($CH_3$)$_2$, $R_2$ is OCO—$(CH_2)_{14}$—$CH_3$, $R_3$ is OCO—$(CH_2)_{10}$—$CH_3$ and $R_4$ is H, or
$R_1$ is CO—CH($CH_3$)—CH($CH_3$)$_2$, $R_2$ is OH, $R_3$ is OCO—$(CH_2)_{10}$—$CH_3$ and $R_4$ is H.

In the present invention, the injenane-type diterpene compound represented by Chemical Formula 2 may be isolated from *Euphorbia kansui* Liou, and preferably from the root area of *Euphorbia kansui* Liou.

In addition to the compound represented by Chemical Formula 2 isolated from *Euphorbia kansui* Liou, the pharmaceutical composition of the present invention may comprise a chemically synthesized compound represented by Chemical Formula 2 or a pharmaceutically acceptable salt thereof.

The present invention comprises not only the compound represented by Chemical Formula 2 and the pharmaceutically acceptable salt thereof, but also all solvates, hydrates or racemates that can be prepared therefrom.

The term "prevention" in the present invention means all actions that suppress viral infectious diseases or delay the outbreak of diseases by the administration of the composition.

The term "treatment" in the present invention means all actions that enable symptoms of viral infection to ameliorate or change for the better by the administration of the composition.

In the present invention, the viral infectious disease may be a disease caused by one or more viruses selected from the group consisting of influenza virus, Influenza A virus subtype H1N1, avian influenza virus, rhinovirus, adenovirus, coronavirus, parainfluenza virus, respiratory syncytial virus, Herpesvirus (HSV), human immunodeficiency virus (HIV), rotavirus and hepatitis virus, but the virus is not limited thereto.

In addition, the viral infectious disease may be one or more viral infectious diseases selected from the group consisting of a rotaviral infectious disease, an adenoviral infectious disease, influenza, cold, a sore throat, bronchitis, pneumonia, avian influenza, eye inflammation, encephalitis, acquired immunodeficiency syndrome, hepatitis and severe acute respiratory syndrome (SARS), but the viral infectious disease is not limited thereto.

The compound represented by Chemical Formula 2 of the present invention may have a form of a pharmaceutically acceptable salt, and as the salt, an acid addition salt formed by a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid or phosphorous acid, and nontoxic organic acids such as aliphatic mono- and dicarboxylate, phenyl-substituted alkanoate, hydroxyalkanoate and alkanedioate, aromatic acids, aliphatic and aromatic sulfonic acids. Such pharmaceutically nontoxic salts comprise sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butene-1,4-dioate, hexane-1,6-dioate, benzoate, chlorobenzoate, methyl benzoate, dinitrobenzoate, hydroxybenzoate, methoxybenzoate, phthalate, terephthalate, benzenesulfonate, toluenesulfonate, chlorobenzenesulfonate, xylenesulfonate, phenyl acetate, phenyl propionate, phenyl butyrate, citrate, lactate, β-hydroxybutyrate, glycolate, malate, tartrate, methanesulfonate, propanesulfonate, naphthalene-1-sulfonate, naphthalene-2-sulfonate or mandelate.

The acid addition salt according to the present invention may be prepared by common methods such as dissolving the compound of Chemical Formula 2 in an excess aqueous acid solution, and precipitating this salt using a water-miscible organic solvent such as methanol, ethanol, acetone or acetonitrile.

In addition, a pharmaceutically acceptable metal salt may be prepared using a base. An alkali metal or alkaline-earth metal salt is obtained by, for example, dissolving the compound in an excess alkali metal hydroxide or alkaline-earth metal hydroxide solution, filtering the non-soluble compound salt, drying the filtrate and drying the result. Herein, preparing a sodium, potassium or calcium salt as the metal salt is pharmaceutically suitable. Furthermore, a silver salt corresponding to this is obtained by reacting the alkali metal or alkaline-earth metal salt with a suitable silver salt (for example, silver nitrate).

The composition of the present invention may comprise a pharmaceutically acceptable carrier. The composition including a pharmaceutically acceptable carrier may have various oral or non-oral formulations. When formulated, the composition is prepared using a filler, an extending agent, a bonding agent, a wetting agent, a disintegrating agent, a diluent such as a surfactant or a diluting agent commonly used. Solid formulations for oral administration comprise tablets, pills, powders, granules, capsules and the like, and these solid formulations are prepared by mixing one or more compounds with at least one or more diluting agents such as starch, potassium carbonate, sucrose or lactose and gelatine. In addition, lubricants such as magnesium stearate and talc are also used in addition to simple diluting agents. Liquid formulations for oral administration comprise suspensions, oral solutions, emulsions, syrups and the like, and various diluting agents such as a wetting agent, a sweetening agent, a flavoring agent and a preserving agent may be comprised therein in addition to commonly used diluents such as water and liquid paraffin. The formulations for non-oral administration comprise sterilized aqueous solutions, non-aqueous solvents, suspensions, emulsions, freeze-dried formulations and suppositories. The non-aqueous solvent and the suspension may comprise propylene glycol, polyethylene glycol, vegetable oil such as olive oil and injectable ester such as ethylolate. As the base of suppository, witepsol, macrogol, tween 61, cacao butter, laurin butter, glycerogelatin and the like may be used.

Meanwhile, the present invention provides a method for preventing or treating viral infectious diseases including administering the composition of the present invention to a subject having a viral infectious disease occurrence or a risk thereof with a therapeutically effective dose.

The term "subject" in the present invention means all animals including human beings already infected or having a possibility to be infected by viruses, and the diseases can be effectively prevented and treated by administering the composition of the present invention to the subject.

The composition of the present invention may be administered in combination with existing therapeutic agents for viral infectious diseases. The composition may be administered through any general path as long as the composition reaches a target tissue. The composition of the present invention may be administered by intraperitoneal administration, intravenous administration, intramuscular administration, subcutaneous administration, intracutaneous administration, oral administration, intranasal administration, pulmonary administration or rectal administration depending on the purpose, but the administration method is not limited thereto. In addition, the composition may be administered by any apparatus capable of moving an active material to a target cell.

The composition of the present invention is administered with a therapeutically effective dose. The term "therapeutically effective dose" means an amount sufficient to treat diseases in a reasonable benefit/risk ratio applicable to medical treatments, and the level of the effective dose may be determined depending on the factors including the types of subjects, severity, age, gender, the types of infecting viruses, the activity of drugs, the sensitivity to drugs, administration time, administration paths and excretion rates, treatment period and drugs simultaneously used, and other factors well-known in the field of medicine. The composition of the present invention may be administered as an individual therapeutic agent or as a combination with other therapeutic agents, and the composition of the present invention may be administered consecutively or simultaneously with existing therapeutic agents. In addition, the composition of the present invention may be administered by single or multiple administration. It is important to administer the amount capable of obtaining a maximum effect with a minimal amount without side effects considering all the factors described above, and the amount may be readily determined by those skilled in the art.

The composition of the present invention may be used for preventing and treating virus infection either alone, or in combination with methods such as surgery, hormone treatments, medication treatments and methods using biologic response modifiers.

In the examples of the present invention, the compound represented by the following Chemical Formula 2, a compound represented by the following Chemical Formula 3, a compound represented by the following Chemical Formula 4 and a compound represented by the following Chemical Formula 5 are isolated from *Euphorbia kansui* Liou, and identified.

[Chemical Formula 2]

[Chemical Formula 3]

[Chemical Formula 4]

[Chemical Formula 5]

In the formulae, $R_1$ is H, $R_2$ is H, $R_3$ is OCO—$(CH_2)_{10}$—$CH_3$ and $R_4$ is CO—$CH(CH_3)$—$CH(CH_3)_2$, $R_1$ is CO—$CH(CH_3)$—$CH(CH_3)_2$, $R_2$ is H, $R_3$ is OCO—$(CH_2)_{10}$—$CH_3$ and $R_4$ is H, $R_1$ is H, $R_2$ is OCO—$(CH_2)_8$—$CH_3$, $R_3$ is H and $R_4$ is H, $R_1$ is CO(CH=CH)—$(CH_2)_4$—$CH_3$, $R_2$ is OAc, $R_3$ is H and $R_4$ is H, $R_1$ is CO—$CH(CH_3)$—$CH(CH_3)_2$, $R_2$ is OCO—$(CH_2)_{14}$—$CH_3$, $R_3$ is OCO—$(CH_2)_{10}$—$CH_3$ and $R_4$ is H, or $R_1$ is CO—$CH(CH_3)$—$CH(CH_3)_2$, $R_2$ is OH, $R_3$ is OCO—$(CH_2)_{10}$—$CH_3$ and $R_4$ is H.

In the present invention, the compound represented by Chemical Formula 2 in which $R_1$ is H, $R_2$ is H, $R_3$ is OCO—$(CH_2)_{10}$—$CH_3$ and $R_4$ is CO—$CH(CH_3)$—$CH(CH_3)_2$ is represented by Compound 1, the compound represented by Chemical Formula 2 in which $R_1$ is CO—CH$(CH_2)$—$CH(CH_2)_2$, $R_2$ is H, $R_3$ is OCO—$(CH_2)_{10}$—$CH_3$ and $R_4$ is H is represented by Compound 2, the compound represented by Chemical Formula 2 in which $R_1$ is H, $R_2$ is OCO—$(CH_2)_8$—$CH_3$, $R_3$ is H and $R_4$ is H is represented by Compound 3, the compound represented by Chemical Formula 2 in which $R_1$ is CO(CH=CH)—$(CH_2)_4$—$CH_3$, $R_2$ is OAc, $R_3$ is H and $R_4$ is H is represented by Compound 4, the compound represented by Chemical Formula 2 in which $R_1$ is CO—$CH(CH_2)$—$CH(CH_2)_2$, $R_2$ is OCO—$(CH_2)_{14}$—$CH_3$, $R_3$ is OCO—$(CH_2)_{14}$—$CH_2$ and $R_4$ is H is represented by Compound 5, the compound represented by Chemical Formula 2 in which $R_1$ is CO—$CH(CH_3)$—$CH(CH_3)_2$, $R_2$ is OH, $R_3$ is OCO—$(CH_2)_{10}$—$CH_3$ and $R_4$ is H is represented by Compound 6, the compound represented by Chemical Formula 3 is represented by Compound 7, the compound represented by Chemical Formula 4 is represented by Compound 8, and the compound represented by Chemical Formula 5 is represented by Compound 9.

The name of Compound 1 is 5-O-(2,3-dimethylbutanoyl)-13-O-dodecanoyl-20-O-deoxyingenol, the name of Compound 2 is 3-O-(2,3-dimethylbutanoyl)-13-O-dodecanoyl-20-O-deoxyingenol, the name of Compound 3 is 20-O-decanoylingenol, the name of Compound 4 is 20-O-acetylingenol-3-O-(2'E,4'Z) decadienate, the name of Compound 5 is gansuiphorin A, the name of Compound 6 is 3-O-(2,3-dimethylbutanoyl)-13-O-dodecanoylingenol, the name of Compound 7 is gansuinine F, the name of Compound 8 is (20R,23E)-eupha-8,23-diene-3b,25-diol, and the name of Compound 9 is euphol.

Figure 10:
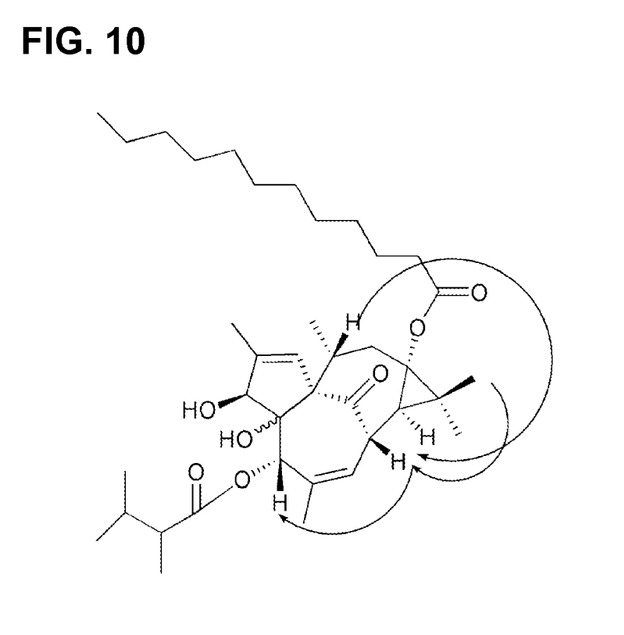
FIG. 10 shows NOESY (↔) correlation of Compound 1.

In the examples of the present invention, the effects of the compounds (1 to 9) on the expression of IFN-γ in NK92 cells were investigated using an ELISA analysis, and it is verified that the compounds 1 to 6 and 8 induce the production of IFN-γ in NK92 cells (FIG. 10). These results show that the compounds 1 to 6 identified in the present invention may be used as useful antiviral agents by facilitating or enhancing the production of IFN-γ in cells.

Furthermore, the present invention provides a health functional food for preventing or ameliorating viral infectious diseases, which comprises the compound represented by Chemical Formula 2 or a sitologically acceptable salt thereof as an active ingredient. In other words, the compound represented by Chemical Formula 2 or the sitologically acceptable salt thereof may be added to foods with the purpose of preventing or ameliorating viral infectious diseases.

In the present invention, "prevention" means all actions that suppress viral infectious diseases or delay the outbreak of diseases by the intake of the health functional foods, and "treatment" means all actions that enable the symptoms of virus infection to ameliorate or change for the better by the intake of the health functional foods.

The health functional food of the present invention comprises all forms such as functional health foods, nutritional supplements, nutritionals, pharmafoods, health foods, nutraceuticals, designer foods, food additives and feed additives.

When the compound of Chemical Formula 2 or the sitologically acceptable salt thereof is added as an additive of a health functional food, the compound or the sitologically acceptable salt thereof may be added either alone or together with other foods or food ingredients, and may be suitably used according to common methods. The amount of mixed active ingredients may be properly determined depending on the purpose of use (use for prevention or amelioration).

The types of the foods are not particularly limited, and examples thereof comprise meat, sausage, bread, chocolate, candies, snacks, cookies, pizza, ramen, other noodles, gums, dairy products including ice creams, various soups, beverages, teas, health drinks, alcoholic beverages and vitamin complexes and the like, and comprise all health functional foods in an accepted meaning.

In addition to the above, the health functional food of the present invention may contain various neutritionals, vitamins, electrolytes, flavoring agents, coloring agents, pectic acid and salts thereof, alginic acid and salts thereof, organic acids, protective colloidal viscosity agents, pH regulating agents, stabilizing agents, preservatives, glycerin, alcohols, carbonating agents used in carbonated beverages and the like.

Furthermore, in addition to these, the health functional food of the present invention may contain flesh for preparing natural fruit juices, fruit juice beverages and vegetable beverages.

The viral infectious diseases are the same as described above.

In addition, the present invention provides a composition for enhancing the production of interferon-gamma, which comprises the compound represented by Chemical Formula 2 or the pharmaceutically acceptable salt thereof as an active ingredient.

The composition for enhancing the production of interferon-gamma may further comprise a pharmaceutically acceptable carrier, and the pharmaceutically acceptable carrier is the same as described above.

In the examples of the present invention, when the compound represented by Chemical Formula 2 is applied to NK92 cells, it was verified that the IFN-γ expression in the NK92 cells increased (FIG. 10). Therefore, the compound represented by Chemical Formula 2 or the pharmaceutically acceptable salt thereof enhances the IFN-γ production in cells, preferably in NK cells, thereby is ultimately useful in preventing or treating viral infectious diseases.

Hereinafter, the constitutions and the effects of the present invention will be described in more detail with reference to examples, however, these examples are for illustrative purposes only, and the scope of the present invention is not limited thereto.

Example 1

Materials and Methods

General Experimental Procedure

The melting point was measured on a Kofler microhostage. The optical rotation was measured using a Jasco P-1020 polarimeter. The UV data were obtained on a UV-VIS spectrometer 2400, and the FT-IR spectra were obtained using a Jasco FT/IR-4200. The NMR spectra were recorded on a Varian UNITY 400 and a Brucker DMX-800 MHz FT-NMR spectrometer using tetramethylsilane as an internal standard material. The HRESIMS and the HRFABMS were carried out on a Waters Q-T of Premier spectrometer and a JEOL JMS-HX110 spectrometer, respectively. The HPLC isolation was carried out on a Gilson pump 305 using a UV/VIS-155 detector.

Plant Material

Roots of *Euphorbia kansui* Liou are an imported product from China, and purchased from Chilsung Corporation, a Korean herb medicine sales company. The standard thereof (PB-3755) is stored in the Plant Extract Bank of the Korea Research Institute of Bioscience and Biotechnology.

Cell Culture

NK92 cells (human NK lymphoma) were obtained from American Type Culture Collection. NK92 cells were kept in α-MEM (Invitrogen, US) containing 20% fetal bovine serum (Invitrogen), 2 mM L-glutamate, 100 mg/mL penicillin and 100 mg/mL streptomycin (Invitrogen), and were replenished with 100 U/mL IL-2 (Peprotech, US). NK92 cell culture was carried out in a culture medium at 37° C. under 5% $CO_2$ humidity atmosphere. The amount of human IFN-γ was analyzed according to the protocol of a supplier using an assay kit (Endogen, Woburn, US).

Example 2

Extraction and Isolation

The MeOH extract (1 kg) of Example 1 was suspended in $H_2O$, and then partitioned to $CHCl_3$, EtOAc, and n-BuOH continuously to give 230.0 g of a $CHCl_3$-soluble extract, 4.5 g of an EtOAc-soluble extract and 41.0 g of an n-BuOH-soluble extract. The $CHCl_3$-soluble fraction was verified to have the highest activity in IFN-γ production. The $CHCl_3$-soluble fraction (100 g) was silica gel column chromatographed using a stepwise concentration gradient mixture of n-hexane:EtOAC (50:1 to 1:1 v/v), and then once again silica gel column chromatographed using a stepwise concentration gradient mixture of CHCl$_3$:MeOH (5:1 to 1:1 v/v) to give 22 fractions (KC16-1 to KC16-22). Next, the material in Fraction KC16-7 was crystallized to give Compound 9 (10 g). Fraction KC16-12 (5.7 g) was chromatographed on a RP C-18 (3.5×40 cm, 40C$_{18}$-PREP) column using a medium pressure liquid chromatography (MPLC) system eluted with MeOH:H$_2$O (4:1 to 4.5:1, and then 100% MeOH) to give 20 fractions (KC16-12-1 to KC16-12-20). Fraction KC16-12-18 (485 mg) was fractioned using Sephadex LH-20 column chromatography (2.5×170 cm) eluted with 90% MeOH in H$_2$O to give 3 fractions (KC16-12-18-1 to KC16-12-18-3). Fraction KC16-12-18-2 (198 mg) was purified through preparative HPLC (YMC J'sphere ODS-H80, 250×20 mm, 4 μm, 100% MeOH, 10 mL/min) using a reversed-phase column to give Compounds 1 (10.0 mg, $t_R$ 13.2 min) and 2 (60.0 mg, $t_R$ 17.1 min). Fraction KC16-12-20 (777 mg) was chromatographed on a silica gel MPLC column eluted with n-hexane:EtOAC (5:1 to 1:1 v/v) to give 8 fractions (KC16-12-20-1 to KC16-12-20-8). Fraction KC16-12-20-1 (366 mg) was fractioned through Sephadex LH-20 column chromatography (2.5×170 cm) eluted with 90% MeOH in H$_2$O to give 4 fractions (KC16-12-20-1-1 to KC16-12-20-1-4). Fraction KC16-12-20-1-2 (100 mg) was purified through preparative HPLC (YMC J' sphere ODS-H80, 250×20 mm, 4 mm, 100% MeOH, 10 mL/min) using a reversed-phase column to give Compound 7 (4 mg, $t_R$ 62.1 min). Active fraction KC16-14 (2.8 g) was chromatographed through MPLC on a RP C-18 column (3.5×40 cm, 40C$_{18}$-PREP) eluted with MeOH:H$_2$O (1:1 to 4.5:1, and then 100% MeOH) to give 18 fractions (KC16-14-1 to KC16-14-18). Fraction KC16-14-10 (153 mg) was chromatographed on silica gel through MPLC column chromatography (3:1 v/v, 3.5×40 cm) eluted with n-hexane:EtOAC to give 4 fractions (KC16-14-10-1 to KC16-14-10-4). Fraction KC16-14-10-1 (36 mg) was purified through preparative HPLC (YMC J' sphere ODS-H80, 250×20 mm, 4 mm, 88% MeOH in H$_2$O, 10 mL/min) using a reversed-phase column to give Compounds 4 (9 mg, $t_R$ 23.5 min) and 5 (4 mg, $t_R$ 32.6 min).

Fraction KC16-14-12 (295 mg) was fractioned using Sephadex LH-20 column chromatography (2.5×170 cm) eluted with 80% MeOH in H$_2$O to give 5 fractions (KC16-14-12-1 to KC16-14-12-5). Fraction KC16-14-12-2 (150 mg) was purified through preparative HPLC (YMC J' sphere ODS-H80, 250×20 mm, 4 mm, 83% MeOH in H$_2$O, 10 mL/min) using a reversed-phase column to give Compound 3 (40 mg, $t_R$ 31.3 min).

Fraction KC16-14-15 (144 mg) was fractioned using Sephadex LH-20 column chromatography (2.5×170 cm) eluted with 80% MeOH in H$_2$O to give 6 fractions (KC16-14-15-1 to KC16-14-15-6). Fraction KC16-14-15-6 (55 mg) was purified through preparative HPLC (YMC 250×20 mm, 4 mm, 70% MeCN in H$_2$O, 10 mL/min) using a reversed-phase column to give Compound 8 (25 mg, $t_R$ 15.4 min).

Fraction KC16-21 (1.2 g) was chromatographed on silica gel through MPLC column chromatography eluted with n-hexane:EtOAC (5:1 to 1:1 v/v, 3.5×40 cm) to give 18 fractions (KC16-21-1 to KC16-21-18). Fraction KC16-21-8 (242 mg) was fractioned using Sephadex LH-20 column chromatography (2.5×170 cm) eluted with n-hexane-dimethyl chloride-MeOH (10:10:1 v/v, 2.5×170 cm) to give 6 fractions (KC16-21-8-1 to KC16-21-8-6). Subfraction KC16-21-8-3 (130 mg) was fractioned using Sephadex LH-20 column chromatography (2.5×170 cm) eluted with 90% MeOH in H$_2$O to give 8 fractions (KC16-21-8-3-1 to KC16-21-8-3-8). Fraction KC16-21-8-3-8 (40 mg) was purified through preparative HPLC (YMC J' sphere ODS-H80, 250×20 mm, 4 mm, 100% MeOH, 10 mL/min) using a reversed-phase column to give Compound 6 (4.5 mg, $t_R$ 12.6 min).

Example 3

Preparation of R- and S-MTPA Ester Derivative of Compound 1

Compound 1 (2.0 mg) was dissolved in 2 mL of anhydrous CH$_2$Cl$_2$. (S)-(+)-α-methoxy-α-(trifluoromethyl)phenylacetyl chloride (3 mL) and N,N-dimethyl-4-aminopyridine were added to the above solution. The mixture was stirred for 24 hours at room temperature. After the reaction was completed, silica gel column chromatography [1×7 cm, n-hexane:EtOAc (15:1)] was carried out on the residue, and an R-MTPA derivative was obtained.

An S-MTPA derivative was prepared using the same procedure except being replaced with other stereoisomer.

Example 4

Compound Identification

Figure 1:
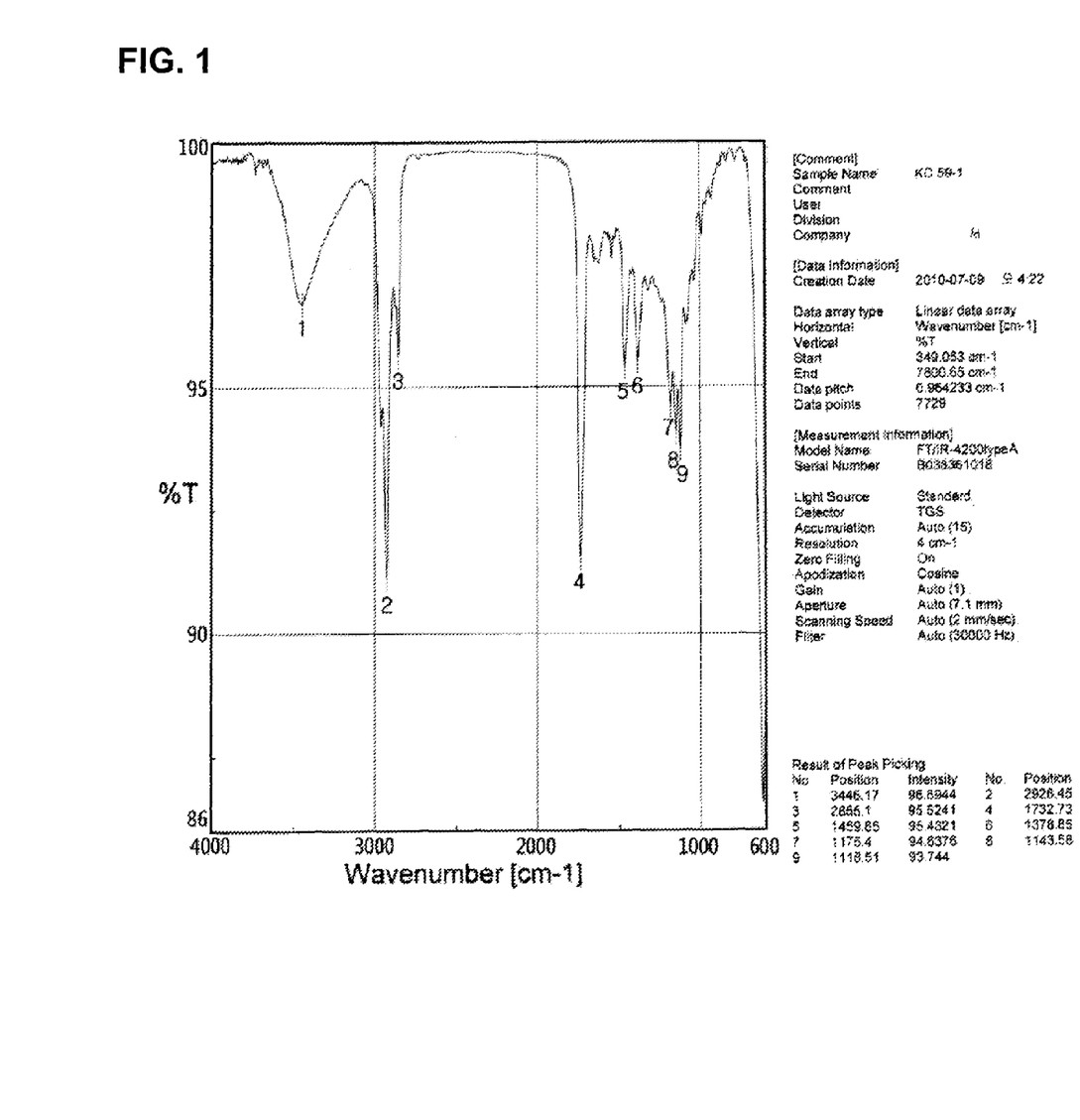
FIG. 1 shows an IR spectrum of Compound 1.
Figure 2:
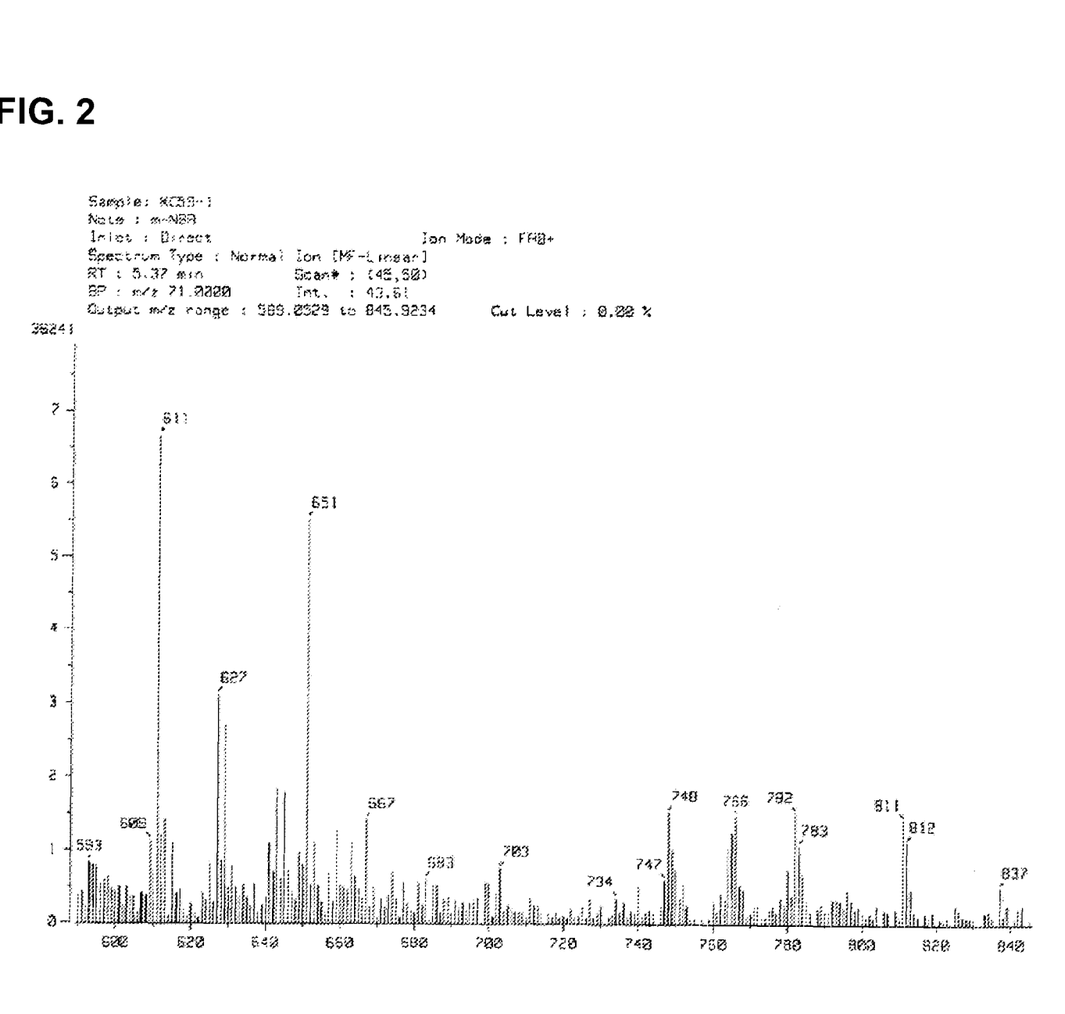
FIG. 2 shows the result of high resolution FABMS of Compound 1.
Figure 3:
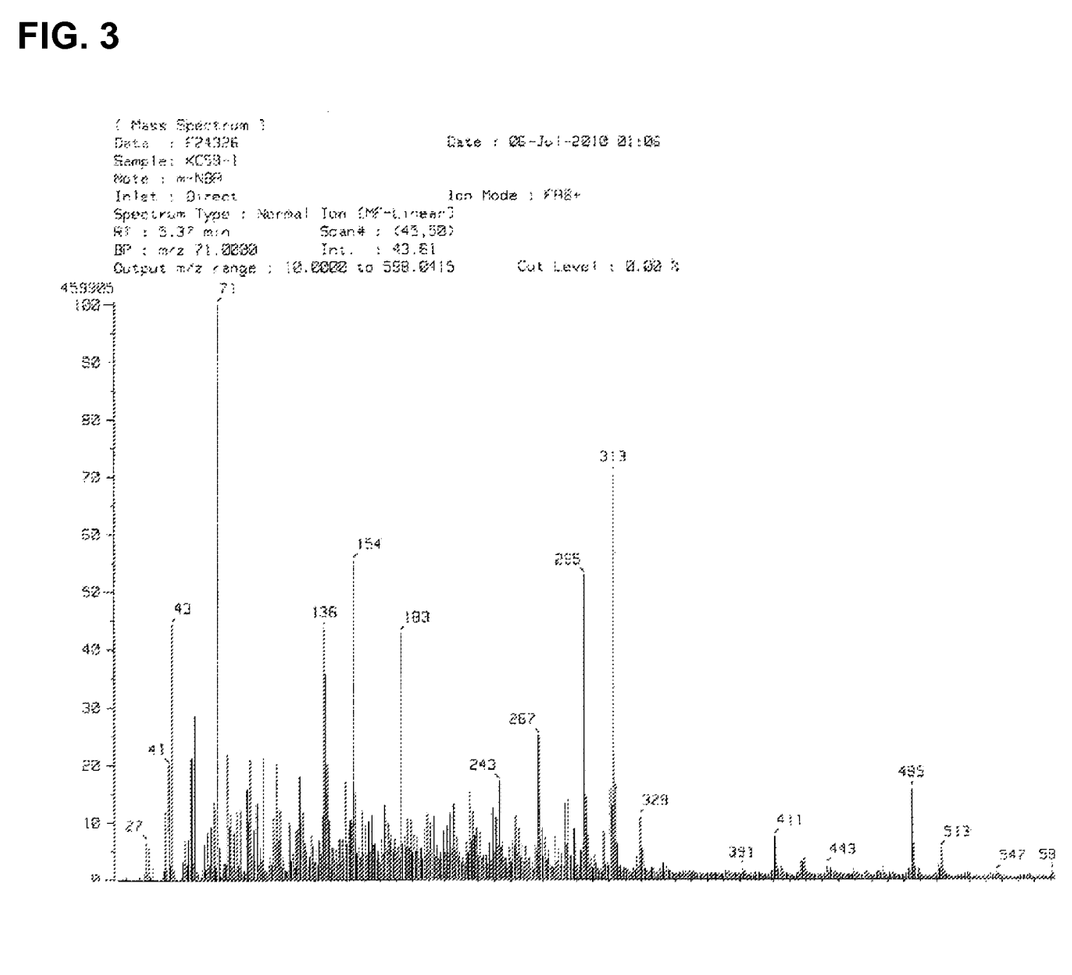
FIG. 3 and FIG. 4 show the result of positive HRFABMS of Compound 1.
Figure 4:
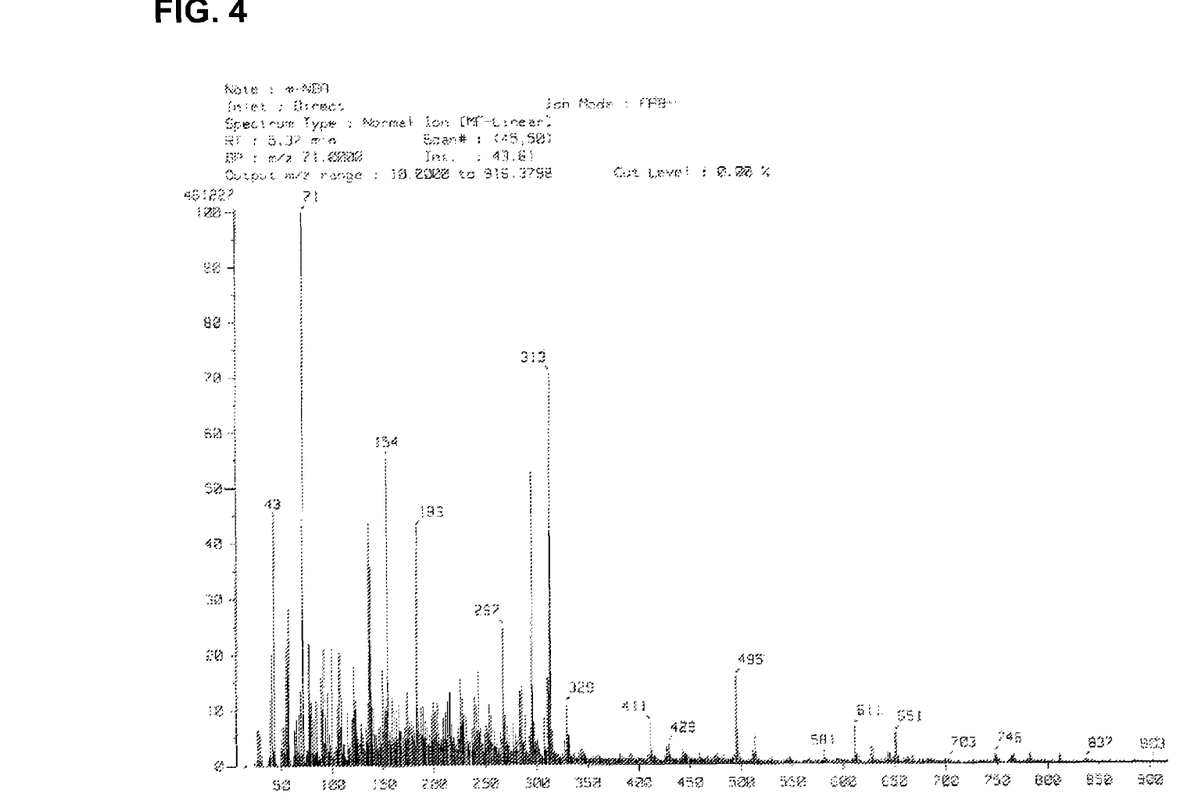
Figure 5:
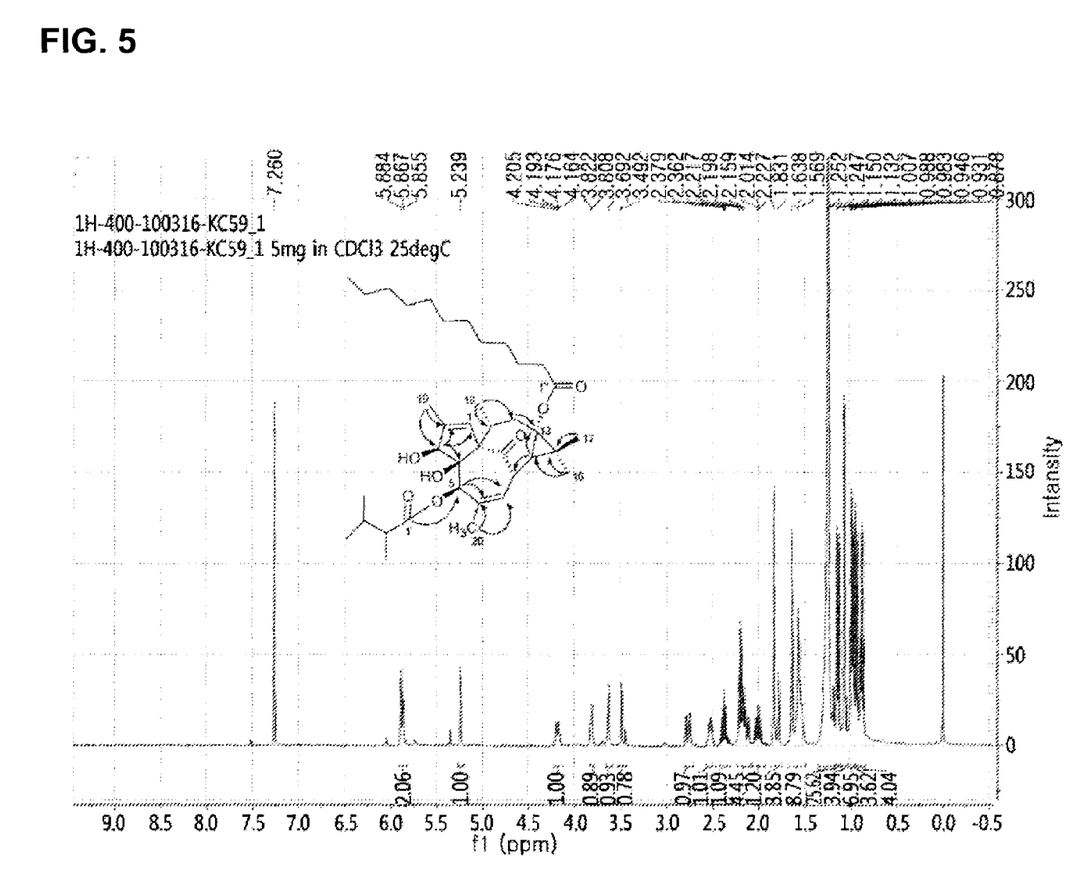
FIG. 5 shows $^1$H-NMR spectroscopic data of Compound 1.
Figure 6:
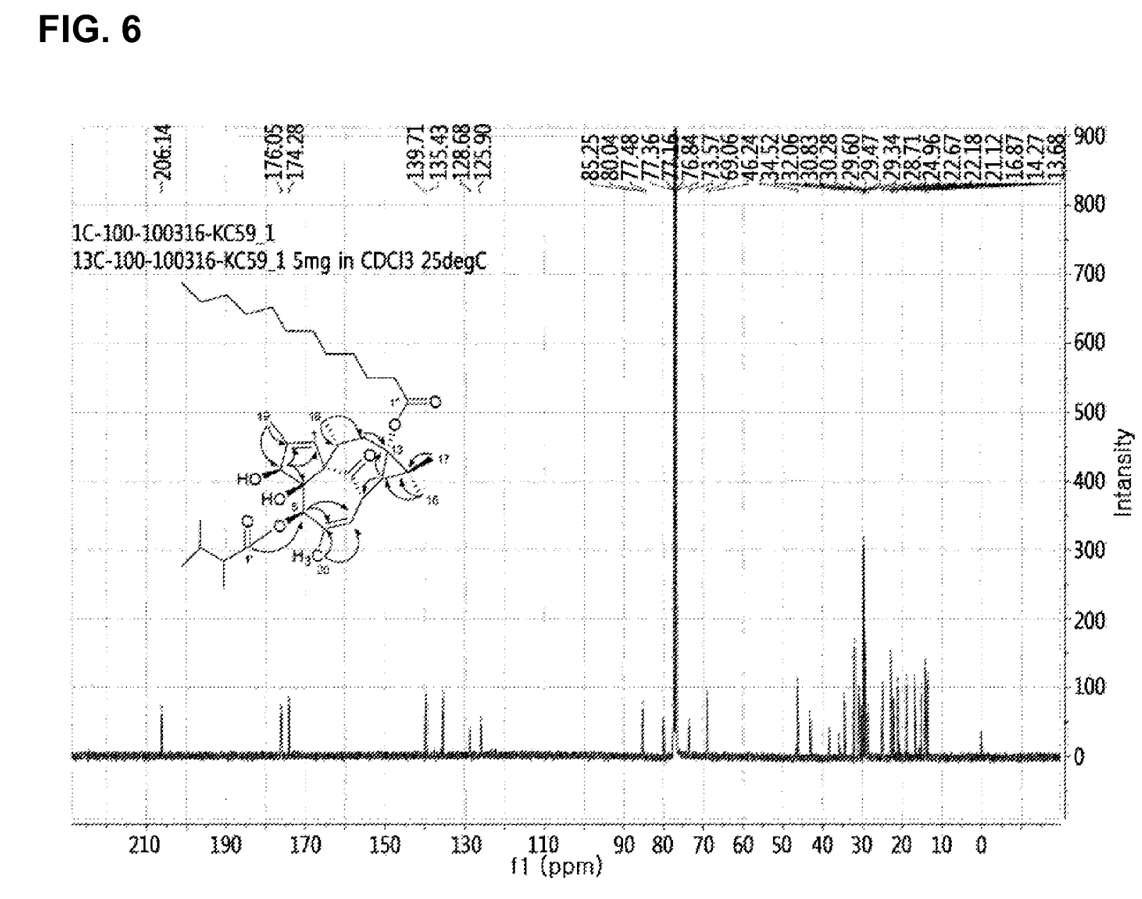
FIG. 6 shows $^{13}$C-NMR spectroscopic data of Compound 1.
Figure 7:
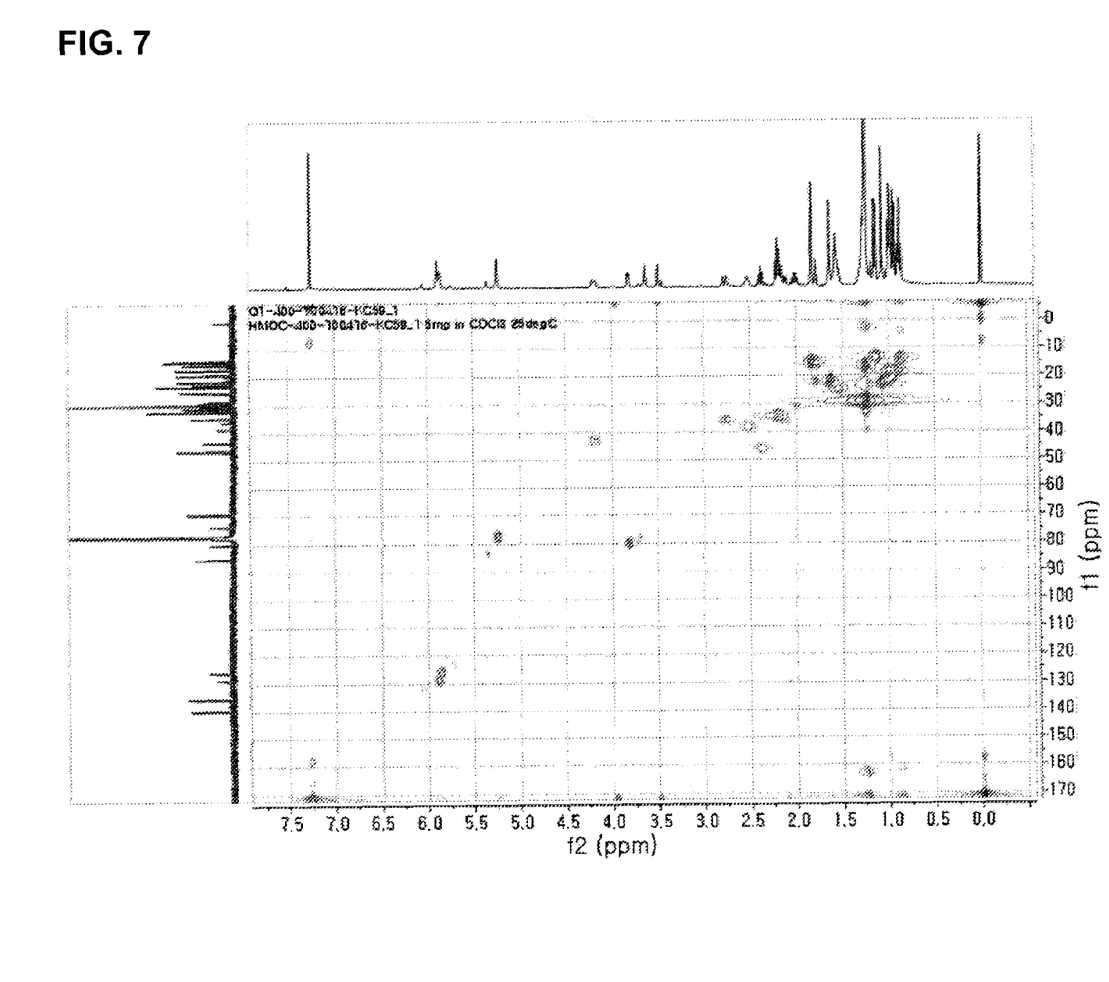
FIG. 7 shows HMQC spectroscopic data of Compound 1.
Figure 8:
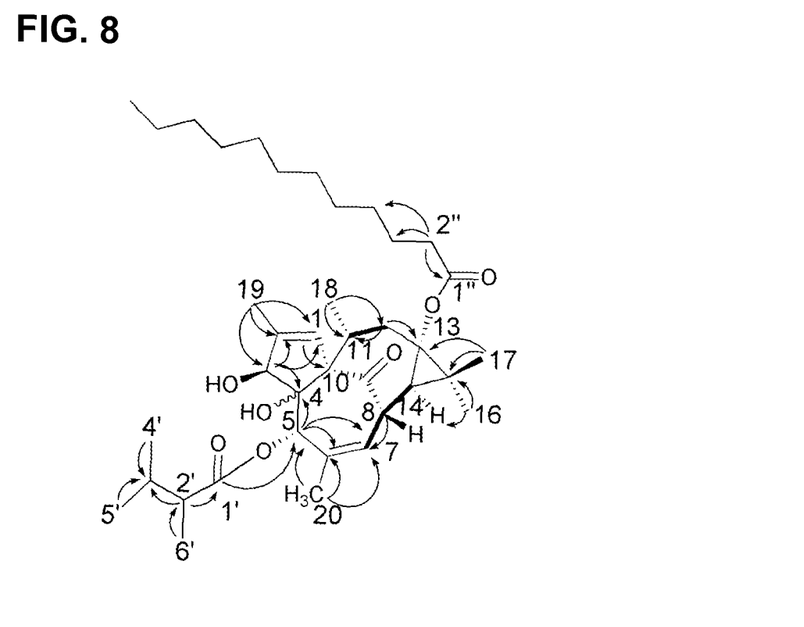
FIG. 8 shows HMBC (H→C) correlation and COSY (H—H) correlation of Compound 1.

Compound 1 was obtained as colorless gum. The IR spectrum thereof showed an absorption band due to the presence of a hydroxyl functional group (3446 cm$^{-1}$) and a carbonyl functional group (1732 cm$^{-1}$) (FIG. 1). The high resolution FABMS of Compound 1 exhibited an [M+Na]$^+$ peak at m/z 651.4271 corresponding to a molecular formula of C$_{38}$H$_{60}$O$_7$ (FIG. 2). In addition, the HRFABMS (positive) of Compound 1 exhibited 2 characteristic ion fragment peaks at m/z 513 [M+H-116]$^+$ and 429 [M+H-200]$^+$ showing the loss of a 2,3-dimethyl butanoate unit and a dodecanoate unit, respectively, from the mother molecule (FIG. 3 and FIG. 4). The $^1$H-NMR spectroscopic data of Compound 1 (FIG. 5) exhibited proton signals at $\delta_H$ 2.38 (1H, m), 2.0 (1H, m), 1.14 (3H, d, J=7.2 Hz), 0.98 (3H, d, J=4.8 Hz), and 0.94 (3H, d, J=6.5 Hz) ppm belonging to the 2,3-dimethylbutanoate group. The dodecanoate spectrum exhibited signals at $\delta_H$ 2.19 (2H, t, J=7.6 Hz), 1.57 (2H, m), 1.25 [overlap signal, 16H], and 0.88 (3H, t, J=6.8 Hz). The rest of the proton signals formed with 5 methyl groups at $\delta_H$ 1.83, 1.64, 1.24, 1.07, and 0.99, 1 methylene group at $\delta_H$ 2.76 and 2.15, 7 methine groups at $\delta_H$ 5.88, 5.85, 4.18, 2.52, and 1.25 (including 2 olefins), and 2 oxygenated methine groups at $\delta_H$ 5.24 and 3.81 was analyzed to be the ingenol-type structure portion. This analysis was additionally supported by the $^{13}$C-NMR (FIG. 6) and the HMQC (FIG. 7) spectroscopic data interpretation. Based on the collected data, it was seen that Compound 1 had partial similarity with 3-O-(2,3-dimethylbutanoyl)-13-O-dodecanoyl-20-O-deoxyingenol (2). The major difference between the two compounds was shown to be the position of 2,3-dimethylbatanoic acid portion. It was verified that the 2,3-dimethylbutanoyl group of Compound 1 was present at C-5 by the HMBC correlation between H-5 ($\delta_H$ 5.24) and C-1' ($\delta_C$ 176.1) (FIG. 8).

Figure 9:
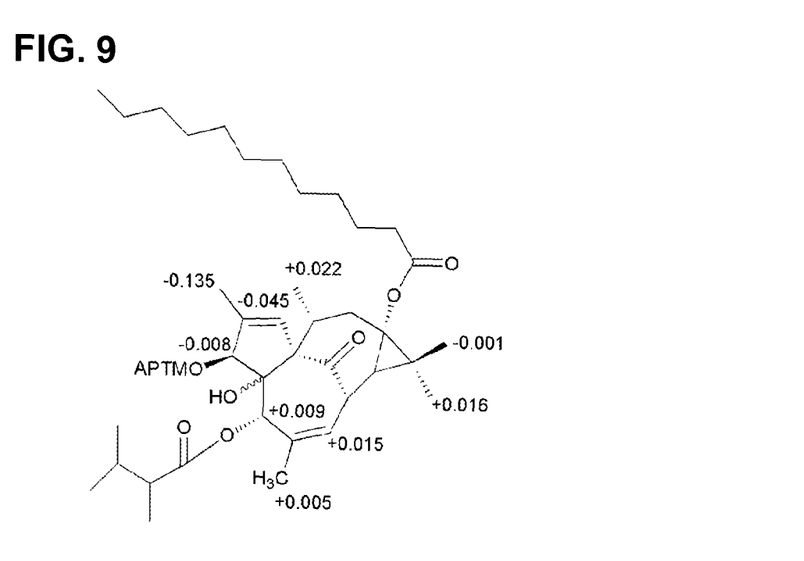
FIG. 9 shows an absolute configuration of Compound 1. Herein, Δδ value ($\delta_S$-$\delta_R$) for 2 MPTA esters 1a and 1b is represented in a hertz unit.

In addition, in order to determine the absolute configuration of C-3 in the structure of Compound 1, a Mosher derivative (1R and 1S) was prepared as in Example 3. As seen in FIG. 9, the difference ($\Delta\delta_{S-R}$) was observed, and the positive value of H-1 and H-19 and the negative value of H-5, H-7, and H-20 clearly demonstrated that the absolute configuration at C-3 was S. As a result, the structure of Compound 1 was verified as (3S)-5-O-(2,3-dimethylbutanoyl)-13-O-dodecanoyl-20-O-deoxyingenol.

Additional experiments were carried out using NOESY in order to identify the absolute stereochemistry of Compound 1. The NOE spectrum showed correlation between H-5, H-20, H-8, H-17, and H-11, and this shows that H-5 is β-oriented. Therefore, the 5-O-(2,3-dimethylbutanoyl)-13-O-dodecanoyl-20-β-deoxyingenol (1) was identified as (3S,5R,16R,17S,18R,19S, 20R) (FIG. 10).

8 additional compounds isolated from the same chloroform extract were each identified as 3-O-(2,3-dimethylbutanoyl)-13-O-dodecanoyl-20-O-deoxyingenol (2), 20-O-decanoylingenol (3), 20-O-acetylingenol-3-O-(2'E,4'Z)decadienate (4), gansuiphorin A (5), 3-O-(2,3-dimethylbutanoyl)-13-O-dodecanoylingenol (6), gansuinine F (7), (20R,23E)-eupha-8,23-diene-3b,25-diol (8), and euphol (9), based on the comparison with open spectroscopic data of the corresponding compounds.

Physicochemical properties and spectroscopic data of Compound 1 were shown below: colorless gum (CHCl$_3$); $[\alpha]^{26}{}_D$ –30° (c 0.1, CHCl$_3$); UV (EtOH) $\lambda_{max}$ nm (log ε) 210 (3.91), 282 (3.08); IR (thin film) cm$^{-1}$: 3346, 1732. FABMS m/z 651 [M+Na]$^+$, 629 [M+H]$^+$, 513 [M+H-116]$^+$, 429 [M+H-200]$^+$, HRFABMS m/z 651.4271 [M+Na] (calculated for C$_{38}$H$_{60}$O$_7$Na, 651.4237).

Furthermore, the $^1$H-NMR (CDCl$_3$) and the $^{13}$C-NMR (CDCl$_3$) data were shown in the following Table 1.

TABLE 1

| Position | $^1$H-NMR | $^{13}$C-NMR |
|---|---|---|
| 1 | 5.88 (1H, s) | 128.7 |
| 2 | | 139.7 |
| 3 | 3.81 (1H, d, J = 5.2) | 80.0 |
| 4 | | 85.3 |
| 5 | 5.24 (1H, s) | 77.4 |
| 6 | | 135.4 |
| 7 | 5.85 (1H, d, J = 5.2) | 125.9 |
| 8 | 4.18 (1H, dd, J = 4.8, 11.6) | 43.2 |
| 9 | | 206.1 |
| 10 | | 73.6 |
| 11 | 2.52 (1H, m) | 38.4 |
| 12a | 2.76 (1H, dd, J = 3.2, 16.8) 2.15 | 35.9 |
| 12b | (1H, m) | |
| 13 | | 69.1 |
| 14 | 1.25 (1H, m) | 28.7 |
| 15 | | 30.3 |
| 16 | 1.07 (3H, s) | 22.7 |
| 17 | 1.24 (3H, brs) | 16.9 |
| 18 | 0.99 (3H, d, J = 5.2) | 18.9 |
| 19 | 1.83 (3H, s) | 15.2 |
| 20 | 1.64 (3H, s) | 22.2 |
| 3-OH | 3.63, s | |
| 4-OH | 3.49, s | |
| 5-R | | |
| 1' | | 176.1 |
| 2' | 2.38 (1H, m) | 46.2 |
| 3' | 2.00 (1H, m) | 30.8 |
| 4' | 0.94 (3H, d, J = 6.5) | 19.0 |
| 5' | 0.98 (3H, d, J = 4.8) | 21.1 |
| 6' | 1.14 (3H, d, J = 7.2) | 13.7 |
| 13-R | | |
| 1" | | 174.2 |
| 2" | 2.19 (2H, t, J = 7.6) | 34.5 |
| 3" | 1.57 (2H, m) | 24.9 |
| 4" | 1.25 (2H, brs) | 29.7 |
| 5" | 1.25 (2H, brs) | 29.7 |
| 6" | 1.25 (2H, brs) | 29.6 |
| 7" | 1.25 (2H, brs) | 29.5 |
| 8" | 1.25 (2H, brs) | 29.4 |
| 9" | 1.25 (2H, brs) | 29.3 |
| 10" | 1.25 (2H, brs) | 32.1 |
| 11" | 1.25 (2H, brs) | 22.8 |
| 12" | 0.88 (3H, t, J = 6.8) | 14.3 |

Example 5

Investigation on IFN-γ Production Capability and Cell Toxicity of Compounds of Present Invention In order to detect IFN-γ, 2×10$^5$ NK92 cell/mL was inoculated in a 48-well culture plate, and was cultured for 12 hours with each isolated compounds in an α-MEM medium containing 20% FBS and IL-2. The IFN-γ released in the culture supernatant was analyzed using an ELISA method. The absorbance was measured on a microplate reader and the treatment and the analysis for all the compounds were repeated twice. The cell toxicity of the compound-treated NK92 cells was evaluated through an MTT analysis.

Figure 11:
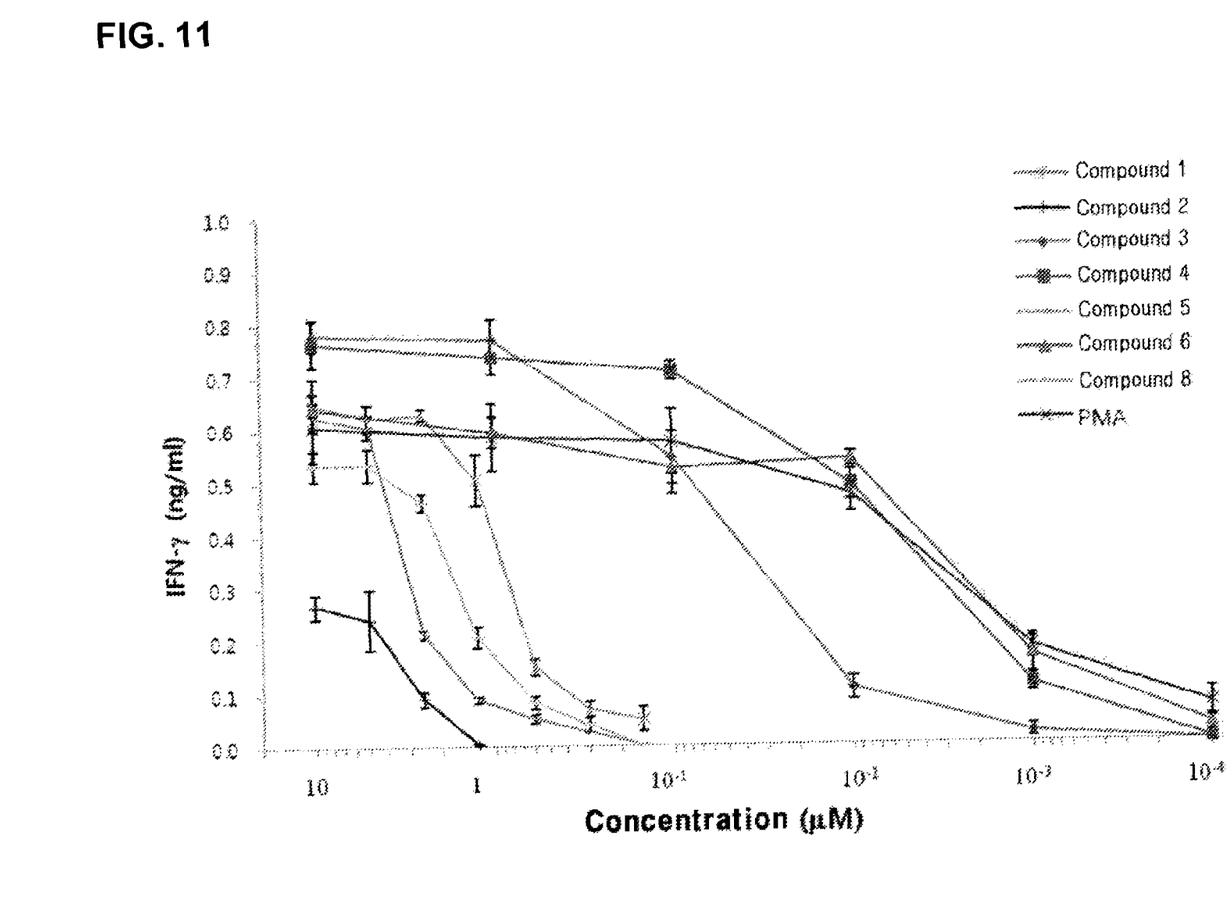
FIG. 11 is a graph showing the effects of Compounds 1 to 6 and 8 on the production of IFN-γ in human natural killer cells (NK92). Herein, phorbol 12-myristate 13-acetate (PMA) is used as a positive control group. Each value is an average±standard deviation value obtained by culture carried out three times.

The results are shown in FIG. 11.

As seen in FIG. 11, it was seen that only Compounds 1 to 6 and 8 induced the production of IFN-γ in NK92 cells. In addition, an effective dose of each compound for IFN-γ production greatly varied. Compounds 4 and 6 (10 nM) were shown to have significant effects on the IFN-γ production, which was similar compared to the same dose of the phorbol 12-myristate 13-acetate (PMA). Compounds 3 (100 nM), 1 (1.25 μM each), 5 and 8 (5 μM each) also had activity for inducing IFN-γ production when treated on NK92 cells. Based on these results, it was verified that the injenane-type diterpene compounds isolated from the root of *Euphorbia kansui* Liou in the present invention are useful as an IFN-γ inducing agent.

The invention claimed is:

1. A method for treating HIV (human immunodeficiency virus) infectious diseases, comprising administering a pharmaceutical composition to a subject having an HIV infectious disease occurrence with a therapeutically effective dose, wherein the composition comprises a compound represented by Chemical Formula 2 or a pharmaceutically acceptable salt thereof as an active ingredient:

[Chemical Formula 2]

wherein, in the formula,
R$_1$ is H, R$_2$ is H, R$_3$ is OCO—(CH$_2$)$_{10}$—CH$_3$ and R$_4$ is CO—CH(CH$_3$)—CH(CH$_3$)$_2$;
R$_1$ is CO—CH(CH$_3$)—CH(CH$_3$)$_2$, R$_2$ is H, R$_3$ is OCO—(CH$_2$)$_{10}$—CH$_3$ and R$_4$ is H;
R$_1$ is H, R$_2$ is OCO—(CH$_2$)$_8$—CH$_3$, R$_3$ is H and R$_4$ is H; or
R$_1$ is CO(CH=CH)—(CH$_2$)$_4$—CH$_3$, R$_2$ is OAc, R$_3$ is H and R$_4$ is H.

2. A method for ameliorating HIV (human immunodeficiency virus) infectious diseases, comprising administering a health functional food to a subject having an HIV infectious disease occurrence, wherein the health functional food comprises a compound represented by Chemical Formula 2 or a sitologically acceptable salt thereof as an active ingredient:

[Chemical Formula 2]

wherein, in the formula,

$R_1$ is H, $R_2$ is H, $R_3$ is OCO—$(CH_2)_{10}$—$CH_3$ and $R_4$ is CO—$CH(CH_3)$—$CH(CH_3)_2$;

$R_1$ is CO—$CH(CH_3)$—$CH(CH_3)_2$, $R_2$ is H, $R_3$ is OCO—$(CH_2)_{10}$—$CH_3$ and $R_4$ is H;

$R_1$ is H, $R_2$ is OCO—$(CH_2)_8$—$CH_3$, $R_3$ is H and $R_4$ is H; or $R_1$ is CO(CH=CH)—$(CH_2)_4$—$CH_3$, $R_2$ is OAc, $R_3$ is H and $R_4$ is H.

3. A method of enhancing production of interferon-gamma in a subject in need thereof, comprising administering a composition to the subject, wherein the composition comprises a compound represented by Chemical Formula 2 or a pharmaceutically acceptable salt thereof as an active ingredient:

[Chemical Formula 2]

wherein, in the formula, $R_1$ is H, $R_2$ is H, $R_3$ is OCO—$(CH_2)_{10}$—$CH_3$ and $R_4$ is CO—$CH(CH_3)$—$CH(CH_3)_2$;

$R_1$ is CO—$CH(CH_3)$—$CH(CH_3)_2$, $R_2$ is H, $R_3$ is OCO—$(CH_2)_{10}$—$CH_3$ and $R_4$ is H;

$R_1$ is H, $R_2$ is OCO—$(CH_2)_8$—$CH_3$, $R_3$ is H and $R_4$ is H;

$R_1$ is CO(CH=CH)—$(CH_2)_4$—$CH_3$, $R_2$ is OAc, $R_3$ is H and $R_4$ is H; or $R_1$ is CO—$CH(CH_3)$—$CH(CH_3)_2$, $R_2$ is OH, $R_3$ is OCO—$(CH_2)_{10}$—$CH_3$ and $R_4$ is H.

* * * * *